United States Patent [19]
Dodey et al.

[11] Patent Number: 6,080,758
[45] Date of Patent: Jun. 27, 2000

[54] BENZENESULFONAMIDE DERIVATIVES AS BRADYKININ ANTAGONISTS

[75] Inventors: Pierre Dodey; Michel Bondoux, both of Fontaine-lès-Dijon; Patrick Houziaux, Bazemont; Martine Barth, Montfort l'Amaury; Khan Ou, Hauteville-lès-Dijon, all of France

[73] Assignee: Fournier Industrie et Sante, France

[21] Appl. No.: 08/817,877

[22] PCT Filed: Aug. 7, 1996

[86] PCT No.: PCT/FR96/01262

§ 371 Date: Apr. 7, 1997

§ 102(e) Date: Apr. 7, 1997

[87] PCT Pub. No.: WO97/07115

PCT Pub. Date: Feb. 27, 1997

[30] Foreign Application Priority Data

Aug. 17, 1995 [FR] France .................... 95 09885

[51] Int. Cl.[7] .............. A61K 31/47; C07D 401/12; C07D 401/14
[52] U.S. Cl. .............. 514/314; 514/211; 514/212; 514/218; 514/222.2; 514/241; 514/253; 514/255; 540/467; 540/470; 540/474; 540/481; 540/545; 540/554; 540/597; 544/363; 544/128; 546/172
[58] Field of Search ............... 546/172; 514/314, 514/253, 255; 544/363, 128; 540/467, 545

[56] References Cited

U.S. PATENT DOCUMENTS 5,563,162 10/1996 Oku ........................ 514/311

OTHER PUBLICATIONS

Stewart JM. Bioplymers. 37, 143–155, 1995.
Stewart JM. Agents and Actions Suppl. 38 (1), 546–550, 1992.

*Primary Examiner*—Evelyn Mei Huang
*Attorney, Agent, or Firm*—St. Onge Steward Johnston & Reens LLC

[57] ABSTRACT

The present invention relates to compounds selected from the group consisting of the compounds of formula (I):

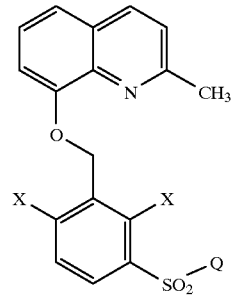

in which Q is

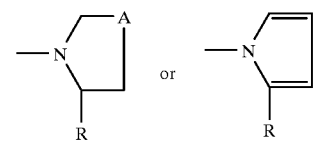

X is a halogen atom, A is $-CH_2-$, $-CH(OH)-$, $-CH(NH-COCH_3)-$ or S, R is H, $CO_2H$, $CO_2-B-R_1$ or $CO-N(R_2)-B-R_1$, B is linear, branched or cyclic $C_1-C_{10}$-alkylene, $R_1$ is H, $CH_2OH$, $CH_2-O-CH_3$, $CH_2-NR_3R_4$ or phenyl, $R_2$ is H or $C_1-C_4$-alkyl, $R_3$ is H or linear, branched or cyclic $C_1-C_{10}$-alkyl, $R_4$ is H or linear or branched $C_1-C_{10}$-alkyl, it being possible for $NR_3R_4$ to be a saturated heterocyclic radical having from 5 to 8 ring members and containing at least one nitrogen atom, and the carbon carrying the substituent R, when Q is saturated, can be of indeterminate (R,S) configuration or of determinate (R) or (S) configuration; and their addition salts. It further relates to their use in therapeutics, especially for pathological conditions involving bradykinin.

12 Claims, No Drawings

BENZENESULFONAMIDE DERIVATIVES AS BRADYKININ ANTAGONISTS

This application is the national phase of PCT/FR96/01262 filed Aug. 7, 1996, published as WO 97/07115 on Feb. 27, 1997.

FIELD OF THE INVENTION

The present invention relates to novel benzenesulfonamide compounds, to the process for their preparation and to their use in therapeutics.

These novel compounds have especially an antagonistic action towards bradykinin and are useful in therapeutics, particularly for the treatment of pain, inflammation, asthma and allergic rhinitis.

PRIOR ART

It is known that one of the possible ways of treating certain pathological conditions of a painful and/or inflammatory nature (such as asthma, rhinitis, septic shock, toothache, etc.) is to antagonize the action of certain hormones such as bradykinin or kallidin. These peptide hormones are in fact involved in a large number of physiological processes, some of which are closely associated with these pathological conditions.

Although no products possessing this mode of action have yet been marketed, numerous studies have been undertaken to create compounds capable of antagonizing the bradykinin receptors. Bradykinin is a peptide hormone consisting of 9 amino acids (Arg-Pro-Pro-Gly-Phe-Ser-Pro-Phe-Arg SEQ ID NO: 1) and kallidin is a peptide hormone (Lys-Arg-Pro-Pro-Gly-Phe-Ser-Pro-Phe-Arg SEQ ID NO: 2) which has an additional amino acid (Lys) compared with bradykinin. Earlier studies are known to have provided peptides which react with the bradykinin receptors: some of them, such as bradycor (CP.0127 from Cortech), icatibant (HOE 140 from Hoechst) ["bradycor" and "icatibant" are international non-proprietary names (INN)] or NPC 17761 (from Scios-Nova), have an inhibitory action on the binding of bradykinin to the bradykinin $B_2$ receptor. More recently, non-peptide compounds have been proposed as bradykinin antagonists in respect of binding to the bradykinin $B_2$ receptor, especially in EP-A-0596406 and EP-A-0622361. It is also known that certain compounds which are structurally related to those referred to in the two patent applications cited above have already been described as possibly having antithrombotic properties, especially in DE-A-3617183 and EP-A-0261539.

OBJECT OF THE INVENTION

There is a need for reducing or eliminating pain and inflammation in mammals and particularly in man.

To meet this need, a novel technical solution has been sought which is effective on the one hand in the treatment of pain, irrespective of its origin, especially pain associated with inflammatory phenomena, and on the other hand in the treatment of inflammation.

According to the invention, it is proposed to provide a novel technical solution which involves competitive binding, at the bradykinin $B_2$ receptor, between (i) bradykinin and related or analogous hormones, and (ii) an antagonistic substance, and utilizes benzenesulfonamide compounds which are structurally different from the known products mentioned above and which limit or substantially inhibit the binding of bradykinin and analogous hormones to said bradykinin $B_2$ receptor.

In accordance with this novel technical solution, it is proposed according to a first feature of the invention to provide benzenesulfonamide compounds as novel industrial products, according to a second feature of the invention to provide a process for the preparation of these compounds, and according to a third feature of the invention to provide the use of these compounds, especially in therapeutics, as analgesic and/or anti-inflammatory active ingredients.

SUBJECT OF THE INVENTION

In accordance with the novel technical solution of the invention, a benzenesulfonamide compound is recommended as a novel industrial product, said compound being characterized in that it is selected from the group consisting of:

(i) the compounds of the formula

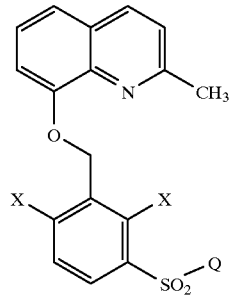

(I)

in which:

X is a halogen atom,

Q is an N-heterocyclic radical of the structure

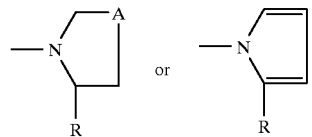

A is a group —$CH_2$—, —CH(OH)— or —CH(NH—$COCH_3$)— or a sulfur atom,

R is a hydrogen atom or a group $CO_2H$, $CO_2$—B—$R_1$ or CO—N($R_2$)—B—$R_1$,

B is a linear, branched or cyclic $C_1$-$C_{10}$-alkylene group, $R_1$ is a hydrogen atom, a group $CH_2OH$, $CH_2$—O—$CH_3$ or $CH_2$—$NR_3R_4$ or a phenyl group, $R_2$ is a hydrogen atom or a $C_1$-$C_4$-alkyl group, $R_3$ is a hydrogen atom or a linear, branched or cyclic $C_1$-$C_{10}$-alkyl group, $R_4$ is a hydrogen atom or a linear or branched $C_1$-$C_{10}$-alkyl group, it being possible for $NR_3R_4$ to be a saturated heterocyclic radical having from 5 to 8 ring members and containing at least one nitrogen atom, and the carbon carrying the substituent R, when Q is saturated, can be of indeterminate (R,S) configuration or of determinate (R) or (S) configuration; and (ii) their addition salts.

According to the invention, a process for the preparation of the compounds of formula I and their addition salts is also recommended.

The use of a substance selected from the compounds of formula I and their non-toxic addition salts is also recommended for obtaining a drug intended for use in therapeutics to combat pathological conditions involving bradykinin or its analogs, in particular to combat pain, and especially in the treatment or prevention of pathological conditions associated with inflammatory or painflil states.

DETAILED DESCRIPTION OF THE INVENTION

In general formula I of the compounds of the invention, halogen atom is understood as meaning a fluorine, chlorine, bromine or iodine atom, the preferred halogen being the chlorine atom as far as the pharmacological or therapeutic activity is concerned.

$C_1$–$C_4$-Alkyl groups are understood here as meaning methyl, ethyl, propyl, 1-methylethyl, butyl, 1,1-dimethylethyl, 1-methylpropyl and 2-methylpropyl groups. Linear, branched or cyclic $C_1$–$C_{10}$-alkylene groups are understood as meaning linear saturated hydrocarbon chains containing between 1 and 10 carbon atoms, branched saturated hydrocarbon chains containing 3 to 10 carbon atoms and hydrocarbon chains whose structure contains at least one saturated ring formed by 3 to 6 carbon atoms.

In formula I the heterocyclic radical Q can be saturated:

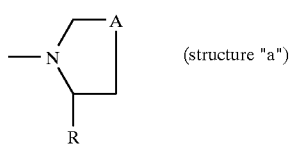

(structure "a")

or unsaturated:

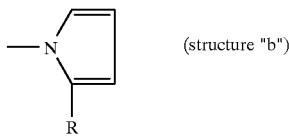

(structure "b")

N-Heterocyclic radical containing at least one nitrogen atom is understood as meaning a saturated cyclic structure containing 5 to 8 ring members (i.e. formed by 5 to 8 atoms), at least one of the atoms in this ring being the nitrogen atom. In practice the ring $NR_3R_4$ can contain a second heteroatom selected from O, N and S and can be substituted especially by a $C_1$–$C_4$-alkyl, $C_1$–$C_4$-ω-hydroxyalkyl, phenyl, 4-methylphenyl or 4-halogenophenyl group. Pyrrolidino, piperidino, 4-methylpiperidino, morpholino, piperazino, 4-methylpiperazin-1-yl, 4-(2-hydroxyethyl)-piperazin-1-yl, 4-phenylpiperazin-1-yl, 4-(4-chlorophenyl)piperazin-1-yl, thiazolidino (or 3-thiazolidinyl), oxazolidino (or 3-oxazolidinyl) and hexamethyleneimino groups may be mentioned in particular among the N-heterocyclic groups $NR_3R_4$ which can be used according to the invention. The preferred N-heterocyclic groups $NR_3R_4$ according to the invention are pyrrolidino, piperidino, 4-methylpiperazin-1-yl, 4-phenylpiperazin-1-yl, thiazolidino, oxazolidino and hexamethyleneimino groups.

"Addition salts" are understood as meaning the acid addition salts obtained by reacting a compound of formula I with a mineral acid or an organic acid. The preferred mineral acids for salifing a basic compound of formula I are hydrochloric, hydrobrornic, phosphoric and sulfuric acids. The preferred organic acids for salifying a basic compound of formula I are methanesulfonic, maleic, fumaric, oxalic, citric and trifluoroacetic acids.

In a first variant A, the process recommended according to the invention for the preparation of the compounds of formula I in which Q is a saturated cyclic radical comprises the steps which consist in:

1) reacting a compound of the formula

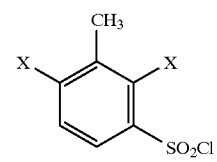

(II)

in which X is a halogen atom, with a halogenating agent, for example N-bromosuccinimide or N-chlorosuccinimide, in a solvent, for example a halogenated hydrocarbon, at a temperature near the reflux temperature of the solvent, in the presence of a free radical initiator, for example benzoyl peroxide, for 0.5 to 5 hours, to give a compound of the formula

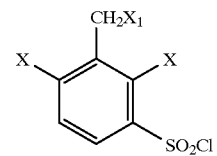

(III)

in which X and $X_1$ are each a halogen;

2) condensing the resulting compound of formula III with a heterocyclic derivative of the formula

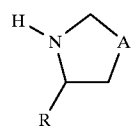

(IV)

in which:

A is a group —$CH_2$—, —CH(OH)— or —CH(NH—$COCH_3$)— or a sulfur atom, and

R is a hydrogen atom, a group $COOCH_3$ or a group $CONHR_3$, in which $R_a$ is a $C_1$–$C_3$-alkyl group, the carbon carrying the substituent R being of (R,S), (R) or (S) configuration, in a solvent, for example dichloromethane, in the presence of a base, for example triethylamine, at a temperature between 0 and 40° C., for 0.5 to 3 hours, to give a compound of the formula

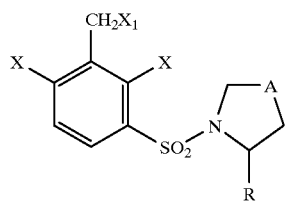

(V)

in which X, A and R are as defined in the starting compounds;

3) reacting the compound of formula V obtained above with a compound of the formula

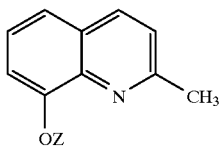

(VI)

in which Z is an alkali metal such as sodium or potassium, in an anhydrous solvent, for example dimethylformnamide or tetrahydrofuran, at a temperature between 0 and 50° C., for 0.5 to 5 hours, to give a compound of the formula

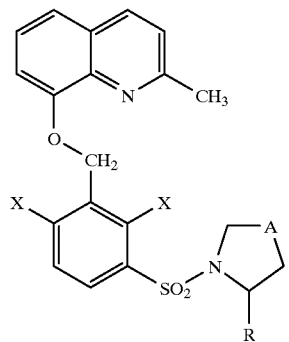

(VII)

in which X, A and R are as defined in the starting compounds and the carbon carrying the substituent R retains the same configuration as in the starting compound IV;

4) if necessary, when R in the compound of formula VII above is an ester group, carrying out alkaline hydrolysis of the ester linkage by reaction with aqueous sodium hydroxide solution in a solvent, for example dimethoxyethane, at a temperature between 10 and 50° C., for 1 to 30 hours, followed by acidification, to give the acid compound of the formula

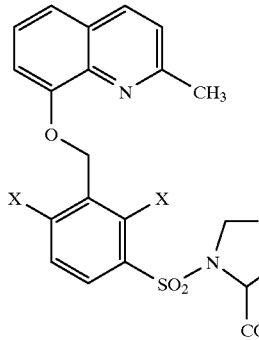

(VIII)

in which X and A are as defined in the starting compound VII; and 5) if necessary, reacting the resulting acid VIII with an alcohol or an amine of the respective formulae HO—B—$R_1$ (IX) or HN($R_2$)—B—$R_1$ (IX')

in which:

B is a $C_1$–$C_{10}$-alkylene chain which is linear or branched or contains a saturated ring, $R_1$ is a hydrogen atom, a group —$CH_2$—O—$CH_3$, a group —$CH_2$—N($CH_3$)$_2$ or a phenyl group, and $R_2$ is a hydrogen atom or a $C_1$–$C_4$-alkyl group, in a solvent, for example dichloromethane, in the presence of activators, for example 1-hydroxy-7-azabenzotriazole (HOAT) and 1-[3-(dimethylaminopropyl)-3-ethyl] carbodiimide hydrochloride (EDCI), at a temperature near room temperature, for 2 to 50 hours, to give a compound of the formula

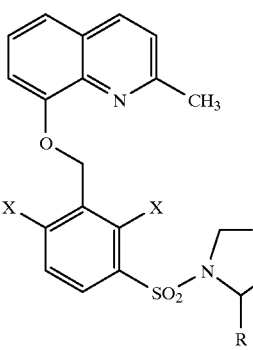

(X)

in which:

X and A are as defined in the starting compounds,

R is a group COO—B—$R_1$ or CO—N(R)—B—$R_1$, in which B, $R_1$ and $R_2$ are as defined in the starting compounds IX or IX', and the carbon carrying the substituent R retains the same configuration as in the starting compound IV.

In a second variant B of the process for the preparation of a compound of formula I in which Q is the pyrrolidino radical, a compound of the formula

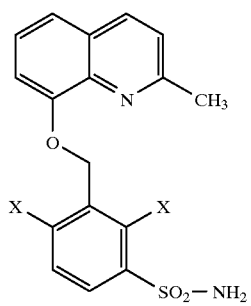

(XI)

in which X is a halogen,
is reacted with 1,4-dibromobutane, in the presence of a base, for example potassium carbonate, in a solvent, for example acetonitrile, at a temperature between 30° C. and the reflux temperature of the solvent, for 3 to 30 hours, to give a compound of the formula

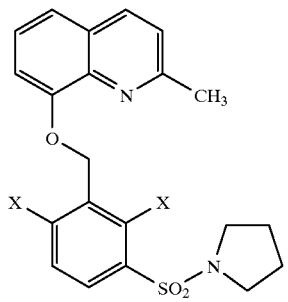

(XII)

BEST MODE

The best mode of carrying out the invention consists in using compounds of formula I and their addition salts in which X is a chlorine atom,
R is a group $CO_2$—B—$R_1$ or CONH—B—$R_1$ in which $R_1$ is $CH_2$—$NR_3R_4$ and B is a $C_1$–$C_{10}$-alkylene group with a saturated linear hydrocarbon chain,
the ring Q is saturated, and
the carbon carrying the substituent R (other than H) is of determinate configuration of the formula

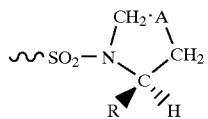

(this structure corresponds to an (S) chiral configuration when A is a group $CH_2$ and to an (R) configuration when A is a sulfur atom).

These compounds are the preferred compounds according to the invention.

The invention will be understood more clearly from the following Preparatory Examples and the results of pharmacological tests obtained with some of the compounds according to the invention. In the case of compounds having an asymmetric carbon in their structure, the absence of a particular indication, or the notation (RS) [or (D,L) in the case of amino acids], means that the compounds are racemic; in the case of compounds which possess chirality, the latter is indicated immediately after the numbering of the substituent carried by said asymmetric carbon; the symbol (R) or (S) is then used in accordance with the Cahn, Ingold and Prelog rules or the notation (D) or (L) is used in the case of amino acids. The nomenclature used in the Examples is that which is recommended by Chemical Abstracts; thus, after reaction of the acid group with an amine, certain L-proline derivatives may become 2-(S)-pyrrolidinecarboxamide derivatives.

In the experimental section the "Preparations" relate to the intermediates and the "Examples" relate to the products according to the invention.

Some of the compounds are characterized by the spectral data obtained by nuclear magnetic resonance (NMR); in this case the spectral characteristics are given for the proton ($^1$H) and the chemical shift of the protons is indicated relative to the proton signal of tetramethylsilane with, in brackets, the shape of the signal (s for singlet, d for doublet, t for triplet, q for quadruplet, m for multiplet, bs for broad signal) and the number of protons corresponding to the signal. By way of indication, the $^1$H NMR spectra were run at 250 MHz.

The melting points (m.p.) indicated below are generally measured using a Koffler bench and are not corrected, so they represent instantaneous melting points.

PREPARATION I

3-Bromomethyl-2,4-dichlorobenzenesulfonyl Chloride 85.44 g (0.48 mol) of N-bromosuccinilnide and then 200 mg of benzoyl peroxide are added to a solution of 41.52 g (0.16 mol) of 2,4-dichloro-3-methylbenzenesulfonyl chloride in 150 ml of 1,1,2,2-tetrachloroethane at room temperature. The reaction mixture is heated at 120° C. for 2 hours. After cooling, it is filtered and the filtrate is washed successively with water, with saturated sodium bicarbonate solution and finally with water until the washings are neutral. The organic phase is then dried over magnesium sulfate and concentrated. The product obtained is crystallized from hexane to give 25.53 g of the expected product in the form of white crystals (yield=47%).
M.p.=90–92° C.

PREPARATION II

3-Chloromethyl-2,4-dichlorobenzenesulfonyl Chloride 10 g (0.075 mol) of N-chlorosuccinimide and 30 mg of benzoyl peroxide are added to a solution of 6.5 g (0.025 mol) of 2,4-dichloro-3-methylbenzenesulfonyl chloride in 30 ml of 1,1,2,2-tetrachloroethane at room temperature and under a nitrogen atmosphere. The reaction mixture is heated at 120° C. for 3 hours, cooled to room temperature, poured into water and then extracted with dichloromethane. The organic phase is washed with water, with saturated sodium bicarbonate solution and finally with water until the washings are neutral. It is then dried over magnesium sulfate and concentrated under reduced pressure. Recrystallization from hexane gives 0.85 g of the expected product in the form of white crystals (yield=11.5%).
M.p.=68° C.

PREPARATION III

N-[(3-Bromomethyl-2,4-dichlorophenyl)sulfonyl]-(D,L)-proline Methyl Ester 27.08 g (0.08 mol) of the compound obtained according to Preparation I are added to a solution of 13.24 g (0.08 mol)

of (D,L)-proline methyl ester hydrochloride in 60 ml of dichloromethane. The mixture is cooled to 0° C. and a solution of 23.3 ml (0.16 mol) of triethylamine in 20 ml of dichloromethane is added dropwise. The reaction mixture is then stirred at room temperature for 30 minutes. It is poured into water and extracted with dichloromethane. The organic phase is washed with 1N hydrochloric acid solution and then with water until the pH is neutral. It is finally dried and concentrated under reduced pressure to give 34.48 g of an oil, which is used directly in the subsequent steps. The product obtained also contains the compound N-[(3-chloromethyl-2,4-dichlorophenyl)sulfonyl]-(D,L)-proline methyl ester, originating from a secondary reaction. As this by-product possesses substantially the same reactivity as the bromine derivative, the mixture is used directly without fuirther purification.

Example 1

N-[[3-[(2-Methylquinolin-8-yl)oxymethyl]-2,4-dichlorophenyl]sulfonyl]-D,L-proline Methyl Ester 0.051 g ($1.7.10^{-3}$ mol) of sodium hydride as an 80% suspension in oil is added to a solution of 0.270 g ($1.7.10^{-3}$ mol) of 8-hydroxy-2-methylquinoline in 5 ml of N,N-dimethylformamide (DMF). After stirring for ten minutes at room temperature, a solution of 0.8 g of the compound obtained according to Preparation III in 2 ml of DMF is added. Stirring is maintained for 2 hours at room temperature. The reaction mixture is diluted with water and extracted with ethyl acetate. The organic phases are washed with water, dried over sodium sulfate, filtered and concentrated under reduced pressure. The residue obtained is purified by chromatography on silica gel using a toluene/ethyl acetate mixture (80/20, v/v) as the eluent. The solid recovered is recrystallized from 15 ml of isopropanol to give 0.7 g of the expected product in the form of a white powder (yield=81%).
M.p.=142° C.

PREPARATION IV

N-[(3-Bromomethyl-2,4-dichlorophenyl)sulfonyl]-L-proline Methyl Ester

The expected product is obtained in the form of an oil by following a procedure analogous to Preparation III, starting from L-proline methyl ester hydrochloride. (The product obtained contains the chlorine analog originating from a secondary halogen exchange reaction.)

Example 2

N-[[3-[(2-Methylquinolin-8-yl)oxymethyl]-2,4-dichlorophenyl]sulfonyl]-L-proline Methyl Ester The expected product is obtained with a yield of 83%, after recrystallization from isopropanol, by following a procedure analogous to Example 1, starting from the compound obtained according to Preparation IV.
M.p.=136° C., $[\alpha]_D^{23}$=+29.40° (c=1.01; CHCl$_3$)

Example 3

N-[[3-[(2-Methylquinolin-8-yl)oxymethyl]-2,4-dichlorophenyl]sulfonyl]-D,L-proline 20 ml ($20.10^{-3}$ mol) of 1N aqueous sodium hydroxide solution are added to a solution of 5.14 g ($10.2.10^{-3}$ mol) of the compound obtained according to Example 1 in 100 ml of 1,2-dimethoxyethane. The reaction mixture is stirred at 40° C. for 1.5 hours and then at room temperature for 20 hours. The mixture is then concentrated under reduced pressure and the residue is taken up with water and acidified to pH 5 with 1N hydrochloric acid. After extraction with dichloromethane, the organic phase is washed with water, dried and concentrated under reduced pressure. The resulting solid is recrystallized from 30 ml of isopropanol to give 4.4 g of the expected product in the form of white crystals (yield=87%).
M.p.=120° C.

Example 4

1-[[3-[(2-Methylquinolin-8-yl)oxymethyl]-2,4-dichlorophenyl]sulfonyl]-N-[2-methoxyethyl]-2-pyrrolidinecarboxamide A solution of 0.495 g ($10^{-3}$ mol) of the acid obtained according to Example 3 in 5 ml of dichloromethane is prepared and 0.21 g ($1.1.10^{-3}$ mol) of 1-(3-dimethylaminopropyl)-3-ethylcarbodiimide hydrochloride (EDCI), 0.15 g ($1.1.10^{-1}$ mol) of 1-hydroxy-7-azabenzotriazole (HOAT) and then 0.15 g ($2.10^{-3}$ mol) of 2-methoxyethanamine are added. The reaction mixture is stirred at room temperature (20–25° C.) for 20 hours and then concentrated under reduced pressure. The residue obtained is purified by chromatography on silica gel using a toluene/isopropanol mixture (9/1, v/v) as the eluent. After recrystallization from a toluene/isopropyl ether mixture (1/8, v/v), 0.34 g of the expected product is obtained in the form of white crystals (yield=61%).
M.p.=107° C.

Example 5

1-[[3-[(2-Methylquinolin-8-yl)oxymethyl]-2,4-dichlorophenyl]sulfonyl]-N-[2-hydroxyethyl]-2-pyrrolidinecarboxamide The expected product is obtained with a yield of 85%, after recrystallization from ethyl acetate, by following a procedure analogous to the process of Example 4, starting from 2-aminoethanol.
M.p.=197° C.

Example 6

1-[[3-[(2-Methylquinolin-8-yl)oxmethyl]-2,4-dichlorophenyl]sulfonyl -N-[3-hydroxypropyl]-2-pyrrolidinecarboxamide The expected product is obtained with a yield of 61%, after recrystallization from ethyl acetate, by following a procedure analogous to the process of Example 4, starting from 3-aminopropanol.
M.p.=147° C.

Example 7

1-[[3-[(2-Methylquinolin-8-yl)oxymethyl]-2,4-dichlorophenyl]sulfonyl]-N-[5-hydroxypentyl]-2-pyrrolidinecarboxamide The expected product is obtained with a yield of 74%, after recrystallization from an ethyl acetate/isopropyl ether mixture, by following a procedure analogous to the process of Example 4, starting from 5-aminopentanol.
M.p.=64° C.

Example 8

1-[[3-[(2-Methylquinolin-8-yl)oxymethyl]-2,4-dichlorophenyl]sulfonyl]-N-[2-dimethylaminoethyl]-2-pyrrolidinecarboxamide Dihydrochloride The expected compound is obtained in the form of the base by following a procedure analogous to the process of Example 4, starting from N,N-dimethylethylenediamine. Said compound is then dissolved in ethyl acetate, after which a solution of hydrogen chloride in ethyl ether is added. The expected dihydrochloride crystallizes and is filtered off (yield=70%).
M.p.=151° C.

PREPARATION V

1-[[3-[(2-Methylquinolin-8-yl)oxymethyl]-2,4-dichlorophenyl]sulfonyl]-N-[3-[(1,1-dimethylethoxycarbonyl)amino]propyl]-2-pyrrolidinecarboxamide The expected product is obtained in the form of a white solid with a yield of 53% by following a procedure analogous to the process of Example 4, starting from 3-[(1,1-dimethylethoxycarbonyl)amino]propanamine.
M.p.=88° C.

Example 9

1-[[3-[(2-Methylquinolin-8-yl)oxymethyl]-2,4-dichlorophenyl]sulfonyl]-N-[3-aminopropyl]-2-pyrrolidinecarboxamide A mixture of 0.7 g ($1.1.10^{-3}$ mol) of the compound obtained according to Preparation V and 0.12 g ($1.1.10^{-3}$ mol) of anisole is prepared and 1.7 ml of trifluoroacetic acid are then added. The solution obtained is stirred for 3 hours at room temperature and then concentrated under reduced pressure. The residue obtained is brought to neutrality with 1N sodium hydroxide solution and the product is extracted with dichloromethane. The organic phase is washed with water, dried and concentrated. The crude product is purified by chromatography on silica gel using a dichloromethane/methanol mixture (8/2, v/v) as the eluent to give 40 mg of the expected product in the form of a beige solid (yield=7.7%).
M.p.=130–132° C.

Example 10

1-[[3-[(2-Methylquinolin-8-yl)oxymethyl]-2,4-dichlorophenyl]sulfonyl]-N-[phenylmethyl]-2-pyrrolidinecarboxamide The expected product is obtained with a yield of 86%, after recrystallization from isopropyl ether, by following a procedure analogous to the process of Example 4, starting from benzylamine.
M.p.=143° C.

Example 11

N-[[3-[(2-Methylquinolin-8-yl)oxymethyl]-2,4-dichlorophenyl]sulfonyl]-D,L-proline 3-(dimethylamino)propyl Ester The expected product is obtained with a yield of 57%, after recrystallization from isopropyl ether, by following a procedure analogous to the process of Example 4, starting from 3-(dimethylamino)propanol.
M.p.=93° C.

PREPARATION VI

1-[[3-(Bromomethyl)-2,4-dichlorophenyl]sulfonyl]-N-ethyl-2-(S)-pyrrolidinecarboxamide The expected product is obtained by following a procedure analogous to the process of Preparation III, starting from N-ethyl-2-(S)-pyrrolidinecarboxamide, and is used directly in the next step.

Example 12

1-[[3-[(2-Methylquinolin-8-yl)oxymethyl]-2,4-dichlorophenyl]sulfonyl]-N-ethyl-2-(S)-pyrrolidinecarboxamide The expected product is obtained with a yield of 72%, after recrystallization from an ethyl acetate/isopropyl ether mixture, by following a procedure analogous to the process of Example 1, starting from the compound obtained according to Preparation VI.
M.p.=80° C., $[\alpha]_D^{25}$=−33.8° (c=1.02; $CH_3OH$)

PREPARATION VII

3-[(1-Oxoethyl)amino]-1-[[3-(bromomethyl)-2,4-dichlorophenyl]sulfonyl]-pyrrolidine The expected product is obtained by following a procedure analogous to the process of Preparation III, starting from 3-(acetylamino)pyrrolidine, and is used directly in the next step.

Example 13

3-[(1-Oxoethyl)amino]-1-[[3-[(2-methylquinolin-8-yl)oxymethyl]-2,4-dichlorophenyl]sulfonyl] pyrrolidine The expected product is obtained with a yield of 48% by following a procedure analogous to the process of Example 1, starting from the compound obtained according to Preparation VII.
M.p.=142° C.

PREPARATION VIII

3-Hydroxy-1-[[3-(bromomethyl)-2,4-dichlorophenyl]sulfonyl]pyrrolidine 0.32 g ($2.95.10^{-3}$ mol) of lutidine and 0.26 g ($2.95.10^{-3}$ mol) of 3-pyrrolidinol are added to a solution of 1 g ($2.95.10^{-3}$ mol) of the compound obtained according to Preparation I in 20 ml of dichloromethane. The mixture is stirred for 3 hours at room temperature and is then poured into 50 ml of 1N hydrochloric acid and extracted with dichloromethane. The organic phase is washed with water and then dried and concentrated. The residue is purified by chromatography on silica gel using a toluene/ethyl acetate mixture (1/1, v/v) as the eluent to give 0.6 g of the expected product. This contains its chloromethyl analog because of a halogen exchange reaction. The product obtained in this way is used directly in the next step.

Example 14

3-Hydroxy-1-[[3-[(2-methylquinolin-8-yl)oxymethyl]-2,4-dichlorophenyl]-sulfonyl]pyrrolidine The expected product is obtained in the form of white crystals with a yield of 76% by following a procedure analogous to the process of Example 1, starting from the compound obtained according to Preparation VIII.

PREPARATION IX

3-[[3-(Bromomethyl)-2,4-dichlorophenyl]sulfonyl] thiazolidine

The expected product is obtained by following a procedure analogous to the process of Preparation HI, starting from thiazolidine, and is used in the next step without further purification.

Example 15

3-[[3-[(2-Methylquinolin-8-yl)oxymethyl]-2,4-dichlorophenyl]sulfonyl]-thiazolidine The expected product is obtained with a yield of 39% by following a procedure analogous to the process of Example 1, starting from the compound obtained according to Preparation IX.
M.p.=130° C.

Example 16

1-[[3-[(2-Methylquinolin-8-yl)oxymethyl]-2,4-dichlorophenyl]sulfonyl]-pyrrolidine A solution of 0.5 g ($0.98.10^{-3}$ mol) of 3-[(2-methylquinolin-8-yloxy)methyl]-2,4-dichlorobenzenesulfonamide in 50 ml of acetonitrile is prepared and 0.5 g ($3.9.10^{-3}$ mol) of potassium carbonate and 0.2 g ($0.98.10^{-3}$ mol) of 1,4-dibromobutane are added. The reaction mixture is heated at the reflux temperature of the solvent for 20 hours and then filtered. The filtrate is concentrated under reduced pressure and the residue is taken up with dilute sodium bicarbonate solution and extracted with dichloromethane. The organic phase is washed with water, dried and concentrated. After the solid residue has been washed with ethyl ether, 0.25 g of the expected product is obtained in the form of a beige solid (yield=62%).
M.p.=204° C.

PREPARATION X

1-[[3-(Bromomethyl)-2,4-dichlorophenyl]sulfonyl]pyrrole

A solution of 0.162 g ($2.4.10^{-3}$ mol) of pyrrole in 2 ml of tetrahydrofuran (THF) is prepared and 0.097 g ($2.4.10^{-3}$ mol) of potassium is added. The reaction medium is heated gently to the reflux temperature of the solvent and is then cooled to room temperature and a solution of 0.82 g of the compound obtained according to Preparation I in 2 ml of THF is added. The reaction medium is subsequently stirred for 12 hours at room temperature and then filtered. The filtrate is then concentrated and the residue obtained is purified by chromatography on silica gel using toluene as the eluent to give 0.190 g of the expected product in the form of a pasty solid (yield=21.3%).
$^1$H NMR (CDCl$_3$): 4.73 (s, 2H); 6.35 (d, 2H); 7.21 (d, 2H); 7.45 (d, 1H); 7.65 (d, 1H).

Example 17

1-[[3-[(2-Methylquinolin-8-yl)oxymethyl]-2,4-dichlorophenyl]sulfonyl]pyrrole The expected product is obtained with a yield of 36% in the form of white crystals by following a procedure analogous to the process of Example 1, starting from the compound obtained according to Preparation X.
M.p.=216–217° C.

The activity of some of the products according to the invention was evaluated in respect of their ability to bind to the bradykinin receptors. Kinins, of which bradykinin is the main representative, actually form a group of small peptides which make a substantial contribution to the inflammatory response and therefore appear to be involved in the pathophysiology of inflammatory diseases. Furthermore, bradykinin is among the most potent analgesics known. Kinins activate two types of receptor, called $B_1$ and $B_2$. The $B_2$ receptor belongs to the large family of receptors with seven transmembrane domains coupled to the G proteins. In the present invention we describe compounds which bind to the $B_2$ receptor and thereby block the binding of bradykinin.

We used the following pharmacological test: Ileum segments are isolated from male guinea-pigs of the Dunkin-Hartley strain (Iffa Credo, l'Arbresle, France) and ground in the following TES buffer: TES 25 mM, 1,10-phenanthroline 1 mM (pH 6.8), bacitracin 140 µg/ml, BSA 1 g/l. The membranes are then isolated by centrifugation (18,000 rpm; 20 min; 4° C.). The binding studies are carried out in the TES buffer using [$^3$H]-bradykinin (120 pM) and 50 µg of membrane protein per test (final volume 500 µl) with an equilibrium time of 90 min at 20° C. The percentage inhibition of the binding of [$^3$H]-bradykinin is then determined in the presence of one of the test compounds according to the invention at a concentration of $10^{-6}$ M.

The results obtained (indicated as "activity") from these tests are collated in Table I below with reference to the Examples given in the description.

The compounds of the present invention which inhibit the binding of [$^3$H]-bradykinin to the guinea-pig $B_2$ receptor (see Table I) also bind to the human $B_2$ receptor cloned and transfected in a stable manner into CHO cells (Chinese Hamster Ovary cells). Thus, in this test, some compounds inhibit the binding of [$^3$H]-bradykinin to the $B_2$ receptor by at least 95% at a concentration of 10 µM.

The compounds of the present invention can be useful in the treatment of pain and particularly in the treatment of numerous pathological conditions involving bradykinin or its homologs. These pathological conditions include septic and hemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angioedema, migraine, cerebrovascular complications, certain neurological disorders, vascular inflammatory states (for example atherosclerosis and arteritis of the lower limbs), painful states (for example toothache, menstrual pain), premature uterine contractions, cystitis and burns.

The compounds of the present invention, which can be used in the form of the free base or in the form of their non-toxic addition salts in association with a physiologically acceptable excipient, will generally be prescribed in therapy at doses of about 1 to 1000 mg/day in a form which can be administered orally, by intravenous, intramuscular or subcutaneous injection, transdermally, by means of aerosols or by means of suppositories.

The compounds may also be administered topically, for example in the form of gels or ointments.

The compounds of the present invention are also useful as pharmacological reagents, especially for the study of hormone-receptor interactions. Use as a pharmacological reagent may require a radiolabeled derivative of one of the compounds according to the invention (for example with tritium [$^3$H] or sulfur [$^{35}$S]) in order to obtain a radioligand intended for conformational studies of the bradykinin $B_2$ receptor or for binding tests involving this type of receptor, for example for the evaluation of novel compounds which are capable of showing an affinity for the bradykinin $B_2$ receptor.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE:
       (A) DESCRIPTION: peptide (v) FRAGMENT TYPE: entire sequence (ix) FEATURE:
       (A) NAME/KEY: bradykinin
       (D) OTHER INFORMATION: see Merck Index, 11th ed.,
           entry 1356

(x) PUBLICATION INFORMATION:
       (A) AUTHORS: Elliott, D.F., et al.
       (B) TITLE: "The Structure of Bradykinin"
       (C) JOURNAL: Biochem. Biophys. Res. Commun.
       (D) VOLUME: 3
       (E) PAGES: 87-91
       (F) DATE: 1960

(xi) SEQUENCE DESCRIPTION: SEQ ID NO: 1:

Arg Pro Pro Gly Phe Ser Pro Phe Arg
1               5

(2) INFORMATION FOR SEQ ID NO:2:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE:
       (A) DESCRIPTION: peptide (v) FRAGMENT TYPE: entire sequence (ix) FEATURE:
       (A) NAME/KEY: kallidin
       (D) OTHER INFORMATION: see Merck Index, 11th ed.,
           entry 5158

(x) PUBLICATION INFORMATION:
       (A) AUTHORS: Nicolaides, E.D., et al.
       (B) TITLE: "The Synthesis of a Biologically
           Active Decapeptide Having the Structure
           Proposed for Kallidin"
       (C) JOURNAL: Biochem. Biophys. Res. Commun.
       (D) VOLUME: 6
       (E) PAGES: 210-216
       (F) DATE: 1961

(xi) SEQUENCE DESCRIPTION: SEQ ID NO: 2:

Lys Arg Pro Pro Gly Phe Ser Pro Phe Arg
1               5                   10

TABLE I

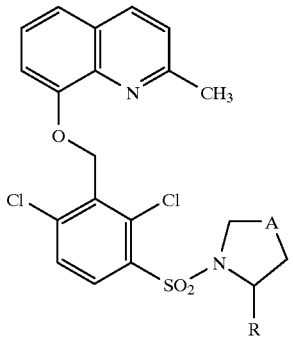

| Ex. No. | A | R | Chirality* | Activity (%) |
|---|---|---|---|---|
| 1 | —CH₂— | —CO₂CH₃ | (R, S) | 97.8 |
| 2 | —CH₂— | —CO₂CH₃ | (S) | 98.6 |
| 3 | —CH₂— | —CO₂H | (R, S) | — |
| 4 | —CH₂— | —CONH—(CH₂)₂—OCH₃ | (R, S) | 92.6 |
| 5 | —CH₂— | —CO—NH—(CH₂)₂—OH | (R, S) | 90.1 |
| 6 | —CH₂— | —CO—NH—(CH₂)₃—OH | (R, S) | 90.9 |
| 7 | —CH₂— | —CO—NH—(CH₂)₅—OH | (R, S) | 97.8 |
| 8** | —CH₂— | —CONH—(CH₂)₂—N(CH₃)₂ | (R, S) | 95.5 |
| 9 | —CH₂— | —CONH—(CH₂)₃—NH₂ | (R, S) | 97.6 |
| 10 | —CH₂— | —CO—NH—CH₂—C₆H₅ | (R, S) | 96.4 |
| 11 | —CH₂— | —COO—(CH₂)₃—N(CH₃)₂ | (R, S) | 76.9 |
| 12 | —CH₂— | —CONH—C₂H₅ | (S) | 98.5 |
| 13 | —CH(NHCOCH₃)— | H | (R, S) | 98.6 |
| 14 | —CH(OH)— | H | (R, S) | 94.0 |
| 15 | —S— | H | — | 94.9 |
| 16 | —CH₂— | H | — | 90.1 |
| 17*** | =CH— | H (pyrrole derivative) | | 93.8 |

Notes:
*The indicated chirality is that of the asymmetric carbon present in the compound; this can be the carbon carrying the substituent R or the carbon included in the group A.
**dihydrochloride.
***the ring Q (cf. general formula I) is pyrrole.

We claim:

1. A compound selected from the group consisting of:

the compounds of the formula

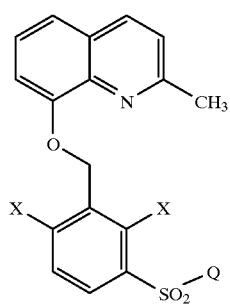

(I)

wherein

X is a halogen atom,

Q is an N-heterocyclic radical of the structure,

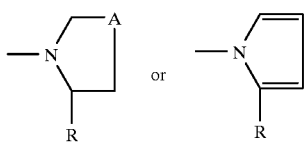

A is a group —CH₂—, —CH(OH)— or —CH(NH—COCH₃)— or a sulfur atom,

R is a hydrogen atom or a group CO₂H, CO₂—B—R₁ or CO—N(R₂)—B—R₁ where

B is a linear, branched or cyclic C₁-C₁₀-alkylene group,

R₁ is a hydrogen atom, a group CH₂OH, CH₂—O—CH₃ or CH₂—NR₃R₄ or a phenyl group,

R₂ is a hydrogen atom or a C₁-C₄-alkyl group,

R₃ is a hydrogen atom or a linear, branched or cyclic C₁-C₁₀-alkyl group,

R₄ is a hydrogen atpm or a linear or branched C₁-C₁₀-alkyl group, or NR₃R₄ is a saturated heterocyclic radical having from 5 to 8 ring members and containing at least one nitrogen atom, and the carbon carrying the substituent R, when the ring Q is saturated, is of indeterminate (R,S) configuration or of determinate (R) or (S) configuration; and their addition salts.

2. A compound according to claim 1 wherein X in formula I is a chlorine atom.

3. A compound according to claim 1 wherein in formula I

X is a chlorine atom,

R is a group $CO_2$—B—$R_1$ or CONH—B—$R_1$ in which $R_1$ is $CH_2$—$NR_3R_4$ and B is a $C_1$-$C_{10}$-alkylene group with a saturated linear hydrocarbon chain, the ring Q is saturated, and the carbon carrying the substituent R (other than H) is of determinate configuration of the formula

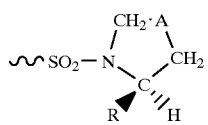

said structure thereby corresponding to an (S) chiral configuration when A is a group $CH_2$ and to an (R) configuration when A is a sulfur atom.

4. A method of treating a pathological condition involving bradykinin or kallidin comprising administering to a mammal in need thereof an effective dose of a drug comprising a substance selected from the group consisting of at least one compound of formula I and their non-toxic addition salts according to claim 1.

5. A method according to claim 4 wherein the drug is for the treatment of pain.

6. A method according to claim 4 wherein the drug is for the treatment of inflammation.

7. A therapeutic composition which comprises:

an amount of at least one compound selected from the group consisting of the compounds of formula I and their non-toxic addition salts according to claim 1 effective to treat a pathological condition involving bradykinin or kallidin; and a physiologically acceptable excipient.

8. A method of using a compound according to claim 1 as a pharmacological reagent for the study of the interaction between bradykinin or kallidin and its receptors comprising binding said compound with receptors for bradykinin or kallidin.

9. A process for the preparation of a compound of formula I of claim 1 in which Q is a saturated cyclic radical, and its addition salts, said process comprising the steps of:

(a) condensing the compound of formula III (III)

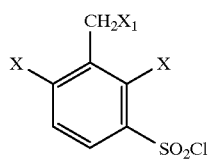

wherein X and $X_1$ are each a halogen atom, with a heterocyclic derivative of the formula (IV)

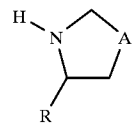

wherein

A is a group —$CH_2$—, a group —CH(OH)—, a group —CH(NH—$COCH_3$)— or a sulfur atom, and R is a hydrogen atom, a group $COOCH_3$ or a group $CONHR_a$, in which $R_a$ is a $C_1$-$C_3$-alkyl group, the carbon carrying the substituent R being of (R,S), (R) or (S) configuration, in a solvent, in the presence of a base, at a temperature between 0 and 40° C., for 0.5 to 3 hours, to give a compound of the formula (V)

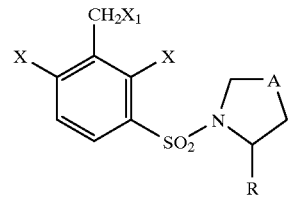

wherein X, A and R are as defined in the starting compounds;

(b) reacting the resulting compound of formula V with a compound of the formula (VI)

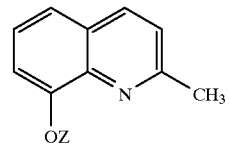

wherein Z is an alkali metal, in an anhydrous solvent, at a temperature between 0 and 50° C., for 0.5 to 5 hours, to give a compound of the formula (VII)

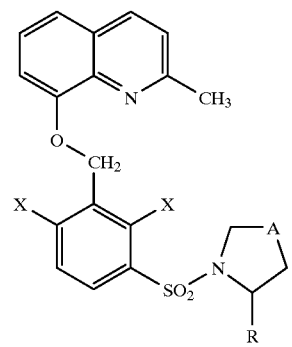

wherein X, A and R are as defined in the starting compounds and the carbon carrying the substituent R retains the same configuration as in the starting compound IV; and (c) if R in the compound of formula VII above is an ester group, carrying out alkaline hydrolysis of the ester linkage in a solvent, at a temperature between 10 and 50° C., for 1 to 30 hours, followed by acidification, to give the acid compound of the formula (VIII)

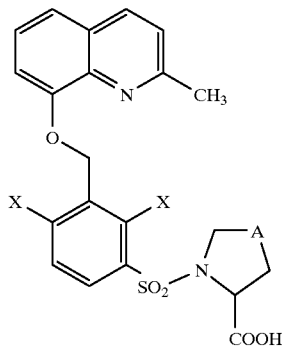

wherein X and A are as defined in the starting compound VII and reacting the resulting acid VIII with an alcohol or an amine of the respective formulae HO—B—R$_1$ (IX) or HN(R$_2$)—B—R$_1$ (IX')

wherein

B is a C$_1$–C$_{10}$-alkylene chain which is linear or branched or contains a saturated ring, R$_1$ is a hydrogen atom, a group —CH$_2$—O—CH$_3$, a group —CH$_2$—N(CH$_3$)$_2$ or a phenyl group, and R$_2$ is a hydrogen atom or a C$_1$–C$_4$alkyl group, in a solvent, in the presence of activators, at a temperature near room temperature, for 2 to 50 hours, to give a compound of the formula (X)

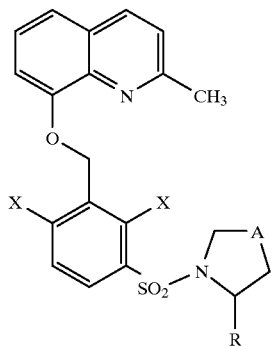

wherein

X and A are as defined in the starting compounds, and

R is a group COO—B—R$_1$ or CO—N(R$_2$)—B—R$_1$ in which B, R$_1$ and R$_2$ are as defined in the starting compounds IX or IX', the carbon carrying the substituent R retaining the same configuration as in the starting compound IV.

10. A process for the preparation of a compound of formula I of claim 1 in which Q is the pyrrolidino radical and its addition salts, said process comprising the step of reacting a compound of the formula (XI)

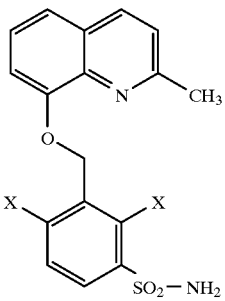

wherein X is a halogen, with 1,4-dibromobutane, in the presence of a base, in a solvent, at a temperature between 30° C. and the reflux temperature of the solvent, for 3 to 30 hours, to give a compound of the formula (XII)

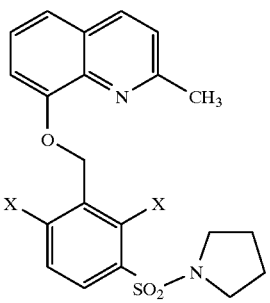

11. A process according to claim 9 wherein the alkali metal of the compound of formula V is sodium.

12. A process according to claim 9 wherein the alkali metal of the compound of formula V is potassium.

* * * * *